(12) United States Patent
Lim et al.

(10) Patent No.: US 10,065,933 B2
(45) Date of Patent: Sep. 4, 2018

(54) METHOD FOR PREPARING GADOBUTROL

(71) Applicant: ST PHARM CO., LTD., Gyeonggi-do (KR)

(72) Inventors: Geun Jho Lim, Gyeonggi-do (KR); Sun Ki Chang, Gyeonggi-do (KR); Chang Ho Byeon, Gyeonggi-do (KR); Hoe Jin Yoon, Gyeonggi-do (KR); Moon Soo Kim, Gyeonggi-do (KR)

(73) Assignee: ST PHARM CO., LTD., Gyeonggi-do (KR)

( * ) Notice: Subject to any disclaimer, the term of this patent is extended or adjusted under 35 U.S.C. 154(b) by 0 days.

(21) Appl. No.: 15/528,281

(22) PCT Filed: Dec. 28, 2015

(86) PCT No.: PCT/KR2015/014301
§ 371 (c)(1),
(2) Date: May 19, 2017

(87) PCT Pub. No.: WO2016/105172
PCT Pub. Date: Jun. 30, 2016

(65) Prior Publication Data
US 2017/0342038 A1    Nov. 30, 2017

(30) Foreign Application Priority Data
Dec. 26, 2014 (KR) .................. 10-2014-0190833

(51) Int. Cl.
*C07D 257/02* (2006.01)
*C07F 5/00* (2006.01)
*A61K 49/10* (2006.01)

(52) U.S. Cl.
CPC .......... *C07D 257/02* (2013.01); *A61K 49/106* (2013.01); *C07F 5/003* (2013.01)

(58) Field of Classification Search
CPC ............................ C07D 257/02; C07F 5/003
See application file for complete search history.

(56) References Cited

FOREIGN PATENT DOCUMENTS

| | | |
|---|---|---|
| JP | H06228115 A | 8/1994 |
| KR | 100269081 B1 | 10/2000 |
| KR | 20130089229 | 8/2013 |
| KR | 20130138807 A | 12/2013 |
| KR | 20140035911 A | 3/2014 |

OTHER PUBLICATIONS

Platzek, J., Blaszkiewicz, P., Gries, H., Luger, P., Michl, G., Muller-Fahrnow, A., Raduchel, B., Sulzle, D., "Synthesis and Structure of a New Macrocyclic Polyhydroxylated Gadolinium Chelate Used as a Contrast Agent for Magnetic Resonance Imaging, Inorganic Chemistry", Jan. 31, 1997, pp. 6086-6093, vol. 36, Issue 26, American Chemical Society, Copyright 1997.

*Primary Examiner* — Noble E Jarrell
(74) *Attorney, Agent, or Firm* — Avery N. Goldstein; Blue Filament Law, PLLC

(57) ABSTRACT

The present disclosure relates to a novel method for preparing high-purity gadobutrol. The present disclosure can be easily applied to a large scale production because purity of intermediate can be managed via simple and mild process and accordingly, high-purity or ultra high-purity gadobutrol that has higher purity than previous gadobutrol can be prepared in high yield therethrough.

14 Claims, No Drawings

METHOD FOR PREPARING GADOBUTROL

TECHNICAL FIELD

The present disclosure relates to a novel method for preparing gadobutrol. Specifically, the present disclosure relates to the method for preparing high-purity gadobutrol by managing purity of intermediate unlike the conventional synthetic methods.

BACKGROUND ART

In field of contrast agents containing gadolinium, gadobutrol is commercially available in the world under brand name of Gadovist or Gadavist.

Gadobutrol represented by Formula 1 below is nonionic complex of microcyclic ligand 10-(2,3-dihydroxy-1-(hydroxymethyl)propyl)-1,4,7,10-tetraazacyclodecane-1,4,7-triacetic acid(butrol) and gadolinium(III), and specifically, it induces shortening of proton relaxation time of tissue fluid in a clinically recommended dose.

[Formula 1]

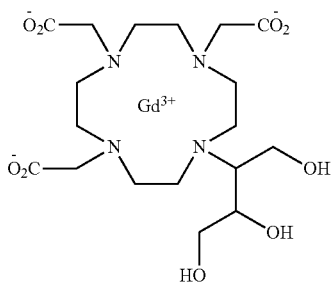

Three routes (schemes 1 to 3) for synthesizing gadobutrol are specifically disclosed in Inorg. Chem. 1997, 36, 6086-6093. The above reference discloses that the route of Scheme 3 is inadequate for a large scale production because of its low yield. Therefore, it is widely known to those skilled in the art that the route of Scheme 3 is only considerable for laboratory scale and it should be avoided for a large scale production. Meanwhile, the Scheme 1 requires large amount of resins for purification and it is disadvantageous because special facilities such as towers and the like should be provided for the purification. Therefore, the method of Scheme 1 is not applicable to large scale production due to increase of unit cost. In addition, the Scheme 2 has problems of low yield and poor purity.

International standards such as ICH Guidelines and the like recommend impurities content to be 0.1% or less, thus it is preferred to prepare ultra high-purity gadobutrol having purity of 99.9% or more for its sales as pharmaceuticals. However, the methods disclosed in the cited reference are complicated and high-purity gadobutrol cannot be prepared therefrom.

Therefore, a novel preparation method, therethrough high-purity gadobutrol can be prepared in high yield with simple preparation process unlike the conventional complicated process, has been required.

The above information disclosed in this Background section is only for enhancement of understanding of the background of the present disclosure and it may therefore contain information that does not form the prior art that is already known to a person of ordinary skill in the art.

DISCLOSURE OF INVENTION

Technical Problem

An object of the present disclosure is to provide a method for preparing high-purity gadobutrol in high yield by a simple and mild process.

Solution to Problem

In order to accomplish the object of the present disclosure, the present disclosure provides a novel method for preparing gadobutrol.

The method of the present disclosure comprises: (S1) preparing a compound of Formula 3 below by using a compound of Formula 2 below or its salt; (S2) preparing a compound of Formula 4 below by using the compound of Formula 3; and (S3) preparing a compound of Formula 1 below by using the compound of Formula 4.

[Formula 1]

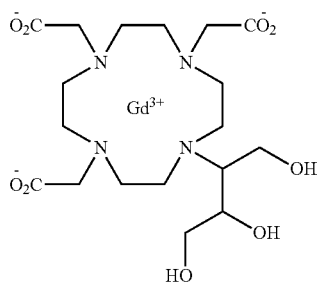

[Formula 2]

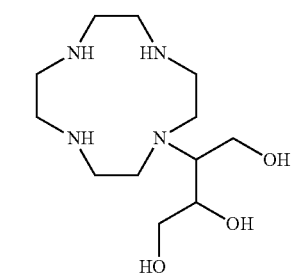 [SMILES: OCC(O)C(CO)N1CCNCCNCCNCC1]

[Formula 3]

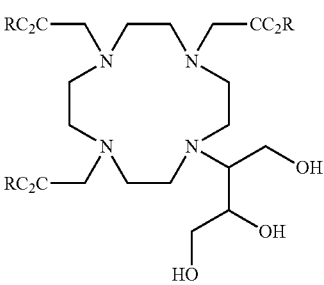

[Formula 4]

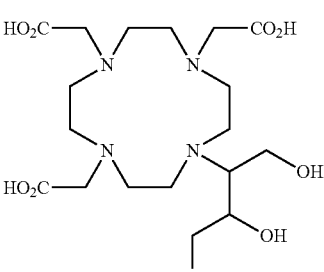

{Wherein, R is linear or branched-chain alkyl of $C_1$-$C_4$}

Each step will be described more fully hereinafter.

(S1): Carboxymethylation

Apropos of the preparation method of the present disclosure, the (S1) step relates to a preparation of the compound of Formula 3 by reacting (i.e. carboxymethylating) the compound of Formula 2 or its salt with a compound of Formula 5 below.

[Formula 5]

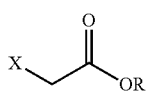

{Wherein, R is linear or branched-chain alkyl of $C_1$-$C_4$ and X is halogen, TsO or MsO}

In some embodiment of the present disclosure, the compound of Formula 2 or its salt in the (S1) step can be 4 hydrochloride of Formula 2-1 below.

[Formula 2-1]

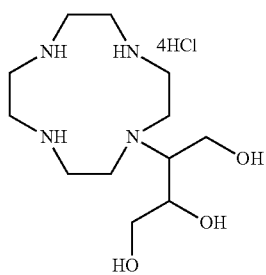

Also, in some embodiment of the present disclosure, the compound of Formula 3 in the (S1) step can be a compound of Formula 3-1 below wherein R is t-Butyl.

[Formula 3-1]

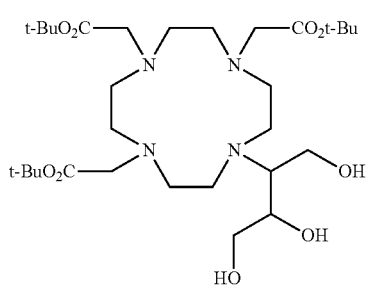

Also, in some embodiment of the present disclosure, the compound of Formula 5 can be a compound of Formula 5-1 below wherein X is Br and R is t-Butyl.

[Formula 5-1]

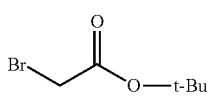

In the (S1) step, the reaction can be performed under the existence of an organic solvent which is commonly used for alkylation (i.e. carboxymethylation) reaction. Preferably, the organic solvent can be a mixed solvent of water and $C_4$-$C_{11}$ ether, and more preferably the organic solvent can be a mixed solvent of water and tetrahydrofuran (THF), but not limited to the above.

Also, the reaction can be performed under the existence of a base, specifically under the existence of an inorganic base. Preferably, the base can be a weak base such as potassium carbonate ($K_2CO_3$), sodium bicarbonate ($NaHCO_3$), potassium bicarbonate ($KHCO_3$) or of mixtures thereof, and more preferably the base can be potassium carbonate but not limited to the above.

The reaction in the (S1) step can be performed at 50 to 80° C., preferably at 65 to 70° C. and more preferably at 63 to 68° C. but not limited to the above.

According to some embodiment of the present disclosure, the (S1) step can further comprise a crystallization process of the compound of Formula 3.

A crystallization solvent used in the crystallization process can be methylene chloride, $C_4$-$C_{11}$ ether, $C_4$-$C_8$ alkane or mixtures thereof, and it is preferable to use a mixture of methylene chloride and n-Hexane.

The compound of Formula 3 can be yielded in high-purity of 99% or more, preferably 99.5% or more, and more preferably 99.7% or more through (S1).

(S2): Acid Hydrolysis

Apropos of the preparation method of the present disclosure, the (S2) step relates to a preparation of the compound of Formula 4 (butrol) in high-purity by performing an acid hydrolysis of the compound of Formula 3 which is yielded in high-purity in the (S1) step.

The acid hydrolysis can be performed by using common reaction condition for acid hydrolysis of ester compound. Preferably, the acid hydrolysis can be performed by adding dilute hydrochloric acid solution or dilute sulfuric acid solution to the compound of Formula 3.

Also, the acid hydrolysis can be performed at 50 to 70° C., preferably at 55 to 65° C., and more preferably at 57 to 63° C., but not limited to the above.

In some embodiment of the present disclosure, the (S2) step can comprises a purification process of the compound of Formula 4 by using resin. Apropos of the present disclosure, amount of the resin is preferably to be about 4 to 8 v/w, and most preferably to be about 5 v/w. Therefore, the preparation method of the present disclosure is advantageous because no additional facilities are required and due to low usage of resin.

Additionally, according to the some embodiment of the present disclosure, the (S2) step can further comprise a crystallization process.

A solvent used in the crystallization process can be methanol, acetone or mixtures thereof, and it is preferable to use a mixed solvent of methanol and acetone.

The compound of Formula 4 (butrol) can be yielded in high-purity of 90% or more, preferably 95% or more, and more preferably 98% or more through (S2).

(S3): Formation of a Gadolinium Complex

Apropos of the preparation method of the present disclosure, the (S3) step relates to a preparation of gadobutrol that is a gadolinium complex by reacting the compound (butrol) of Formula 4 prepared in high-purity in the (S2) step with a gadolinium ion source.

The gadolinium ion source can be any compounds that can supply gadolinium ion. It can be gadolinium oxide, gadolinium acetate or gadolinium chloride. Preferably, the gadolinium ion source can be gadolinium oxide but not limited to the above.

The reaction in the (S3) step can be performed at 80 to 100° C., preferably at 85 to 95° C., and more preferably at 87 to 93° C., but not limited to the above.

The (S3) step can further comprise a crystallization process of gadobutrol.

The compound of Formula 1 (gadobutrol) can be yielded in high-purity of 99% or more, preferably 99.5% or more, and more preferably 99.9% or more through the (S3) step.

In some embodiment of the present disclosure, gadobutrol can be prepared through a method represented by Scheme 1 below.

[Scheme 1]

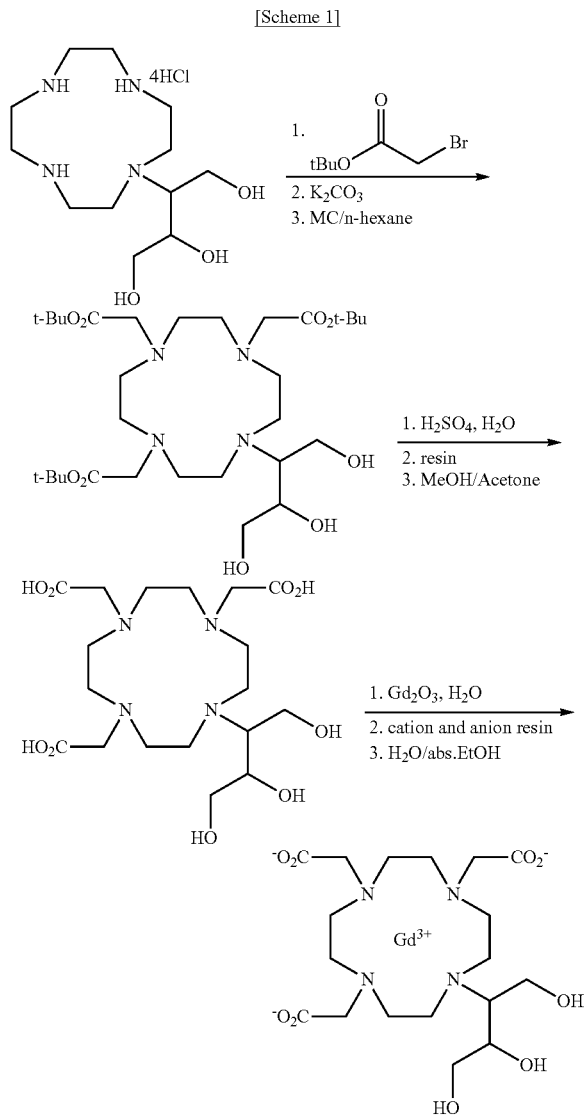

Advantageous Effects of Invention

The preparation method of the present disclosure enables high yield production of high-purity gadobutrol by only a simple and mild process.

BRIEF DESCRIPTION OF DRAWINGS

The present disclosure will be described more fully hereinafter with reference to the accompanying examples. However, the present disclosure may be embodied in many different forms, and should not be construed as being limited to the examples set forth herein.

In addition, reagents and solvents disclosed hereinafter were purchased from Sigma-Aldrich Korea unless otherwise said, IR was measured by using Jasco's FT-IR 4100 series; HPLC was measured by using Agilent Technoliges 1200 Series; and 1H NMR was measured by using Varian Mercury Instrument's oxford NMR 300 MHz Spectrometer. Purity was calculated as area % of HPLC.

EXAMPLE 1

Step 1: Preparation of tertbutyl-2,2',2''-(10-(1,3,4-trihydroxybutan-2-yl)-1,4,7,10-tetraazacyclododecan-1,4,7-triyl)triacetate 3-(1,4,7,10-tetraazacyclododecan-1-yl)butan-1,2,4-triol 4 hydrochloride (100 g, 0.2368 mol) was dissolved under stirring in 500 ml of purified water and 1500 ml of tetrahydrofuran. Potassium carbonate (327 g, 2.3684 mol) was added thereto at room temperature and tert-butylbromoacetate (143.2 g, 0.434 mmol) was slowly added thereto. Upon completion of the addition, a reaction was performed at 63 to 68° C. When the reaction was terminated, 1000 ml of purified water was added thereto and stirred, and then an aqueous layer was separated. The solvent of separated organic layer was removed by concentrating under reduced pressure and then an organic layer was separated by using 1500 ml of purified water and 1000 ml of toluene. An aqueous layer was separated by adding 550 ml of hydrochloric acid to the organic layer. 500 ml of methylene chloride was added to the separated aqueous layer and pH was adjusted to 9.3 to 9.8 by using 100 g of sodium carbonate, and then an organic layer was separated therefrom. The separated organic layer was washed with 10% salt water to separate the organic layer and dehydration was performed, and then the solvent was concentrated under reduced pressure. 400 ml of methylene chloride and 1600 ml of n-hexane were added to the concentrated residue and the resulting solid therefrom was filtered and dried to prepare 117.3 g of tertbutyl-2,2',2''-(10-(1,3,4-trihydroxybutan-2-yl)-1,4,7,10-tetraazacyclododecan-1,4,7-triyl)triacetate.

Yield: 80%, Purity: 99.7%

$^1$H-NMR (CDCl$_3$, 300 MHz): δ(ppm) 1.46 (s, 9H), 1.90~3.10 (m, 11H), 3.20~3.80 (m, 17H)

Infrared spectrum (KBr, cm$^{-1}$): 3350, 2980, 2960, 2860, 2820, 1730, 1455

Step 2: Preparation of 2,2',2''-(10-(1,3,4-trihydroxybutan-2-yl)-1,4,7,10-tetraazacyclododecan-1,4,7-triyl)triacetic acid (butrol)

Internal temperature was raised to 57~63° C. while tertbutyl-2,2',2''-(10-(1,3,4-trihydroxybutan-2-yl)-1,4,7,10-tetraazacyclododecan-1,4,7-triyl)triacetate (30 g, 0.048 mol) prepared in Step 1 was dissolved under stirring in 60 ml of purified water. After elevating the temperature, a mixed solution of 60 ml of purified water and 6 ml of sulfuric acid prepared in advance was added drop-wise. A reaction was performed for 4 hours at the same temperature and cooled to room temperature (20 to 25° C.) upon confirming termination of the reaction. When the cooling was completed, the same was treated with resin (5 v/w) and concentrated. 90 ml of methanol and 300 ml of acetone were added to the concentrated residue and resulting crystal was washed with acetone. The filtered crystal was dried in vacuo at internal temperature of 50° C. to prepare 20.1 g of 2,2',2"-(10-(1,3,4-trihydroxybutan-2-yl)-1,4,7,10-tetraazacyclododecan-1,4,7-triyl)triacetic acid.

Yield: 92%, Purity: 98%

$^1$H-NMR (CDCl$_3$, 300 MHz): δ(ppm) 1.92~3.15 (m, 11H), 3.23~3.88 (m, 17H)

Infrared spectrum (KBr, cm$^{-1}$): 3350, 2980, 2960, 2860, 2820, 1730, 1455

Step 3: Preparation of Gadolinium Complex (Gadobutrol) of 10-(2,3-dihydroxy-1-(hydroxymethyl)propyl)-1,4,7,10-tetraazacyclododecan-1,4,7-triacetic acid 2,2',2"-(10-(1,3,4-trihydroxybutan-2-yl)-1,4,7,10-tetraazacyclododecan-1,4,7-triyl)triacetic acid (15.4 g, 0.0342 mol) prepared in Step 2 was dissolved under stirring in 77 ml of purified water, and gadolinium oxide (8.67 g, 0.0240 mol) was added thereto. Internal temperature was raised to 87~93° C. and the same was stirred for 1 hour at the same temperature. After confirming termination of the reaction, the reaction solution was filtered by using diatomite. Resin was added to the filtrate and stirred, then filtered. The same was decolorated and concentrated under reduced pressure. 7.7 ml of purified water was added to the concentrated residue and the same was stirred for 2 hours at internal temperature of 70 to 75° C. After termination of the dissolution, 121.5 ml of ethanol was added thereto and refluxed under stirring for 3 hours. The same was cooled to room temperature (20 to 25° C.), stirred for 1 hour at the same temperature and filtered under nitrogen atmosphere. The filtered crystal was dried in vacuo at internal temperature of 50° C. or less to prepare 16.2 g of gadolinium of 10-(2,3-dihydroxy-1-(hydroxymethyl)propyl)-1,4,7,10-tetraazacyclododecan-1,4,7-triacetic acid.

Yield: 78.3%, Purity: 99.99%

Infrared spectrum (KBr, cm$^{-1}$): 3560, 3280, 2980, 2975, 2940, 2920, 2880, 2870, 1650, 1600, 1380

COMPARATIVE EXAMPLE 1

Gadobutrol was prepared according to Scheme 1 disclosed in the conventional art (Inorg. Chem. 1997, 36, 6086-6093).

Yield: 65%, Purity: 95.98%

Infrared spectrum (KBr, cm$^{-1}$): identical to Example 1.

COMPARATIVE EXAMPLE 2

Gadobutrol was prepared according to Scheme 2 disclosed in the conventional art (Inorg. Chem. 1997, 36, 6086-6093).

Yield: 63%, Purity: 93.57%

Infrared spectrum (KBr, cm$^{-1}$): identical to Example 1.

Those skilled in the art will appreciate that the conceptions and specific embodiments disclosed in the foregoing description may be readily utilized as a basis for modifying or designing other embodiments for carrying out the same purposes of the present disclosure. Those skilled in the art will also appreciate that such equivalent embodiments do not depart from the spirit and scope of the disclosure as set forth in the appended Claims.

INDUSTRIAL APPLICABILITY

The preparation process of the present disclosure is very adequate for a large scale production because the process is very mild and high-purity gadobutrol can be prepared in high yield by simple process.

The invention claimed is:

1. A method for preparing gadobutrol comprising:
   (S1) preparing a compound of Formula 3 below by using a compound of Formula 2 below or its salt;
   (S2) preparing a compound of Formula 4 below by using the compound of Formula 3; and
   (S3) preparing a compound of Formula 1 below by using the compound of Formula 4 where Formula 1:

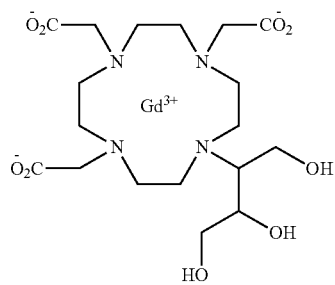

Formula 2:

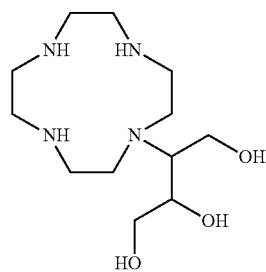

Formula 3:

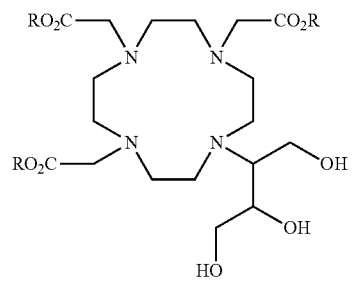

Formula 4:

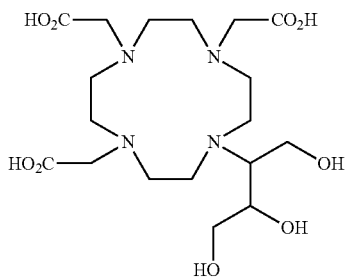

and where R is linear or branched-chain alkyl of $C_1$-$C_4$.

2. The method according to claim 1, the (S1) step comprises reacting the compound of Formula 2 with a compound of Formula 5 below under existence of a mixed solvent of water and $C_4$-$C_{11}$ ether and an inorganic base where Formula 5:

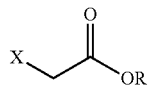

And where R is identical with claim 1 and X is halogen, $TsO^-$ or $MsO^-$.

3. The method according to claim 2, the ether is tetrahydrofuran (THF).

4. The method according to claim 2, the inorganic base is potassium carbonate ($K_2CO_3$), sodium bicarbonate ($NaHCO_3$), potassium bicarbonate ($KHCO_3$) or mixtures thereof.

5. The method according to claim 2, the (S1) step further comprises a crystallization process.

6. The method according to claim 5, a crystallization solvent used in the crystallization process is methylene chloride, $C_4$-$C_{11}$ ether, $C_4$-$C_8$ alkane or mixtures thereof.

7. The method according to claim 6, the crystallization solvent is a mixture of methylene chloride and n-Hexane.

8. The method according to claim 1, the salt of the compound of Formula 2 in the (S1) step is 4 hydrochloride of Formula 2-1 below where Formula 2-1:

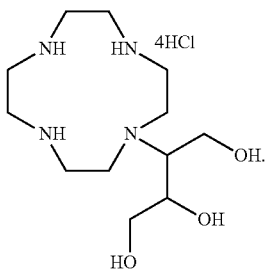 [SMILES: OCC(O)C(CO)N1CCNCCNCCNCC1]

9. The method according to claim 1, the compound of Formula 3 in the (S1) step is a compound of Formula 3-1 below where Formula 3-1:

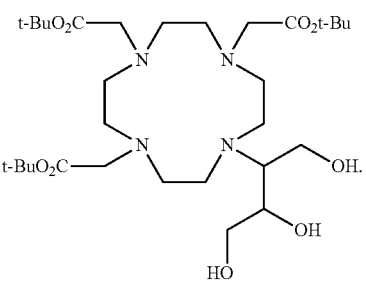

10. The method according to claim 1, the (S2) step is performed by an acid hydrolysis.

11. The method according to claim 10, the (S2) step comprises a purification process of the compound of Formula 4 by using resin.

12. The method according to claim 11, the (S2) step further comprises the crystallization process.

13. The method according to claim 12, wherein a solvent used in the crystallization process is methanol, acetone or mixture thereof.

14. The method according to claim 1, the gadolinium ion source is gadolinium oxide, gadolinium acetate or gadolinium chloride.

* * * * *